United States Patent [19]

Manning

[11] 4,436,819
[45] Mar. 13, 1984

[54] ETHYLENE OXIDE PROCESS DOSIMETER

[75] Inventor: Charles R. Manning, Los Altos, Calif.

[73] Assignee: Assay Tec Associates, Inc., Los Altos, Calif.

[21] Appl. No.: 354,496

[22] Filed: Mar. 3, 1982

[51] Int. Cl.³ .............................................. G01N 21/78
[52] U.S. Cl. .......................................... 436/1; 422/56; 422/87; 436/93; 436/902
[58] Field of Search ....................... 422/55, 56, 57, 58, 422/83, 86, 87; 436/1, 93, 902, 169

[56] References Cited

U.S. PATENT DOCUMENTS

| | | | |
|---|---|---|---|
| 3,627,469 | 12/1971 | Cheng | 422/56 X |
| 3,852,034 | 12/1974 | Gunther | 436/1 |
| 4,094,642 | 6/1978 | Sumimoto et al. | 436/1 X |
| 4,195,056 | 3/1980 | Patel | 422/56 |

OTHER PUBLICATIONS

Alfrey, Jr. et al., Journal of Polymer Science: Part C No. 12, pp. 249–261, (1966), "Diffusion in Glassy Polymers".

Primary Examiner—Arnold Turk
Attorney, Agent, or Firm—Burns, Doane, Swecker & Mathis

[57] ABSTRACT

A device for chemically quantifying ethylene oxide exposure is disclosed as are methods for its use. The device comprises an ethylene oxide-permeable layer exhibiting unusual non-Fickian EO transport and containing a controlled amount of compound which forms a colored species upon reaction with ethylene oxide. Optionally, the response layer is laminated or otherwise joined with a support layer. The device can be used to quantify in industry accepted units of time and concentration sterilization dosages of ethylene oxide.

13 Claims, 7 Drawing Figures

ONE-LAYER DEVICE

TWO-LAYER DEVICE

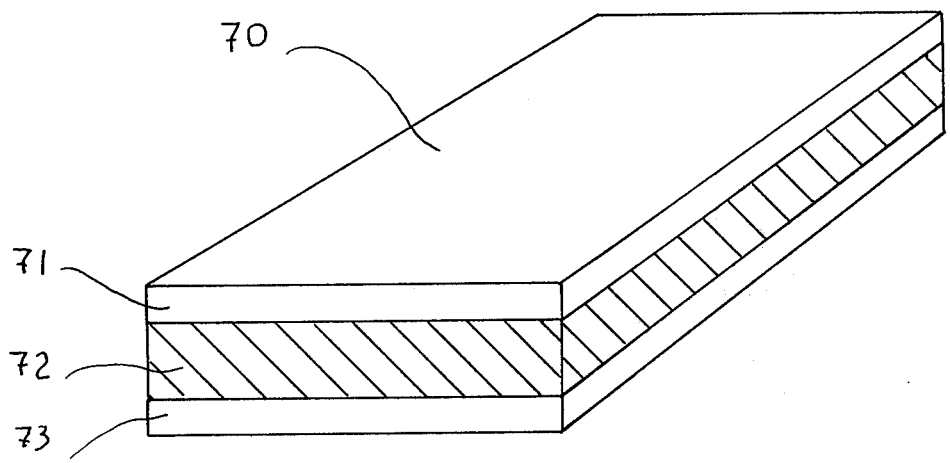

ETHYLENE OXIDE PROCESS DOSIMETER

BACKGROUND OF THE INVENTION

1. Field of the Invention

This invention relates to devices for quantifying chemical exposure and/or content. More particularly, it relates to devices for quantifying ethylene oxide and methods for their use.

2. Background

Ethylene oxide (EO) is widely used as a chemical reactant and as a sterilizing agent whose toxic efficacy is dose-dependent. Accordingly, it is of interest to have available methods or devices to measure the degree of sterilizing dose which has been applied to an article to be sterilized. For quality assurance purposes, it is desired to have a method or device that can express ethylene oxide exposure in industry accepted numerical terms of concentration and time. Since EO is toxic, it is also of interest to have available a method for determining EO residual levels in plastics after sterilization.

The device described herein is characterized as being a true dosimeter for ethylene oxide exposure rather than merely an indicator of exposure.

In the context of medical, industrial, and forensic science, the most crucial decisions are made daily on the basis of measurement (analysis of quantity, mass, extent, or degree in terms of a standard unit of measure), whereas mere indication (demonstration of the probable presence or nature of) can only be used as corroborative evidence.

In the context of measurement science, a "true dosimeter" is a device which measures the integral over time of chemical concentration (i.e. time-average concentration), usually specified in the International System (SI) of Units as: $[(Mass) \times (Time) \div (Volume)]$, e.g. g-hour/l.

The present devices are dosimeters that measure a true ethylene oxide dose (concentration-time integral), and can for that matter, report the dose as an analytically measured result in unambiguous units referenced to a primary standard (e.g., g-hour/l referenced to the International System (SI) of Units).

Comparison With Prior Art

Various means have been described in open and patent literature for indicating exposure of medical or other articles to ethylene oxide sterilizing mixtures. The use of 4-(p-nitrobenzyl) pyridine as a color-forming reagent which reacts specifically to alkylating agents has been disclosed in Anal. Chem., 27, 1435 (1955); and 33, 906 (1961) and J. Pharm. Sci., 55, 57 (1961). A variety of other amines, including pyridines, quinolines, and other heterocyclic compounds, as well as anilines, diphenylamines, and related materials have been shown to exhibit color formation or color change as a result of exposure to ethylene oxide. Representative references include U.S. Pat. Nos. 2,998,306; 3,000,706; 3,258,312; 3,627,469; 3,667,917 and 4,015,937.

The great majority of means described in patent literature for indicating exposure to ethylene oxide (such as the patents just noted) are mere indicators, that is, they indicate, by the appearance of a color, that exposure to ethylene oxide has taken place. These devices serve a purpose in indicating that individual packages have actually passed through a sterilizer but are not equivalent to the device of this application which measures a quantitative sterilizing dose.

Similarly, U.S. Pat. Nos. 3,738,811 and 3,992,154 describe devices for indicating the presence or absence of EO in sterilized goods.

In U.S. Pat. Nos. 3,852,034, 3,992,154 and 4,094,642 devices have been described which purport to indicate by a telltale indicator whether or not exposure dose sufficient to exercise a sterilizing effect has occurred. These devices, while claiming additional function, have severe disadvantages as follows: (a) whereas the sterilizing dose required is known to vary with the nature of the article sterilized and its native microbial burden, these devices must be pre-set to exhibit a telltale in response to a single exposure dose; (b) since they do not read out in units of measure, they are not correlatable with established physical-chemical process parameters; (c) since they respond to an arbitrary but unspecified extent of processing, they are not usable for demonstrating that packages have passed throught the sterilizer, since for many articles a sterilizing dose could be achieved without these devices exhibiting their telltale response.

More rarely, as in U.S. Pat. Nos. 4,138,216 and 4,145,186, devices are described which purport to demonstrate the actual degree of exposure dose presented in a sterilizing chamber. While these devices do report quantitative results of exposure dose they have two disadvantages (a) These devices report out in arbitrary units of gauge displacement and the user must correlate gauge readings with sterilization process parameters; (b) the disclosed devices are complex assemblies of an inherently greater size and cost than the biological indicators which they are meant to replace, limiting their use in routine quality assurance.

The EO exposure measuring devices described herein read out in pre-calibrated physical-chemical units (for example, g-hr/l of EO exposure @ standard temperature) allowing immediate correlation with extensive data in the open literature relating g/l of EO, hours of time, and degrees of temperature to sterilizing efficacy. The residual EO measuring devices described herein read out in precalibrated physical-chemical units (for example, mg of EO), as well. These devices can be employed at significantly lower cost than biological indicators, with greater precision, and with no requirement for special user expertise. The design and manufacturing bases disclosed herein allow manufacture of membrane, film, and sheet compositions which can be prepared and joined by continuous processing, then cut to size without costly molding, assembly, or attaching steps.

STATEMENT OF THE INVENTION

I have now discovered a device and method for its use that permits the ready quantification of ethylene oxide exposure and content by physical-chemical means. The device of my invention, in its simplest form, comprises an ethylene oxide-diffusive transparent polymer substrate of a material defined herein as permitting "Case II" ethylene oxide transport in which is dispersed a reproducible concentration of a compound which is reactive with ethylene oxide and which undergoes a color change as a result of its reaction with ethylene oxide.

In use, to measure exposure, this device is placed in an ethylene oxide-containing environment, such as a sterilizing environment, usually in accompanyment with articles being sterilized at a measured temperature. In use to measure residual EO contents, the device is sealed in an ethylene oxide-impermeable container with the article being measured and heated. Thereafter, the device is removed from the environment and its color is determined visually or spectroscopically and compared to colors produced by standard exposures of the same material to known times and concentrations of ethylene oxide. As the rate of color change is predictably dependent upon temperature the standard exposures preferably are made at or about the test temperature. Alternatively, exposures may be determined in a temperature-variant environment as equivalent g-hr/l of ethylene oxide exposure at the standard temperature. Other aspects of my invention will become apparent to those skilled in the art by their reading of the accompanying DESCRIPTION OF PREFERRED EMBODIMENTS and appended claims.

BRIEF DESCRIPTION OF THE DRAWINGS

In this specification, reference will be made to the drawings which accompany it. In the drawings:

FIGS. 5, 6, 7 are three pictorial views of three embodiments of the device of this invention.

DESCRIPTION OF PREFERRED EMBODIMENTS

The device of this invention collects and measures exposure such as sustained as a result of application of ethylene oxide sterilizing or fumigating processes. Alternately, it measures the EO volatilized in a confined space from residual-bearing materials.

By a sorption-diffusion mechanism, the device collects ethylene oxide gas, in a quantity directly proportional to the immediate, local ethylene oxide concentration and directly proportional to the duration of exposure. At a fixed temperature, the total quantity collected thus reflects the Time-Average-Ethylene Oxide Concentration integrated over the duration of exposure i.e., $\int_0^t C dt$, where: C=EO concentration; t=exposure time).

By appropriate chemical reaction with a colorimetric agent in the device, a characteristic color is generated within the device whose intensity is directly proportional to the quantity of ethylene oxide collected and hence to the product of Time×Average×Concentration.

In contrast to prior art ethylene oxide-monitoring devices, a true dosimeter will have a response directly proportional to the first power of ethylene oxide concentration and to the first power of exposure time. Only such a first order response to both concentrations and time can result in equivalent readings for all concentration-time curves having the same integrated concentration-time product $$\left( \int_0^t C dt \right).$$

Figure 1:
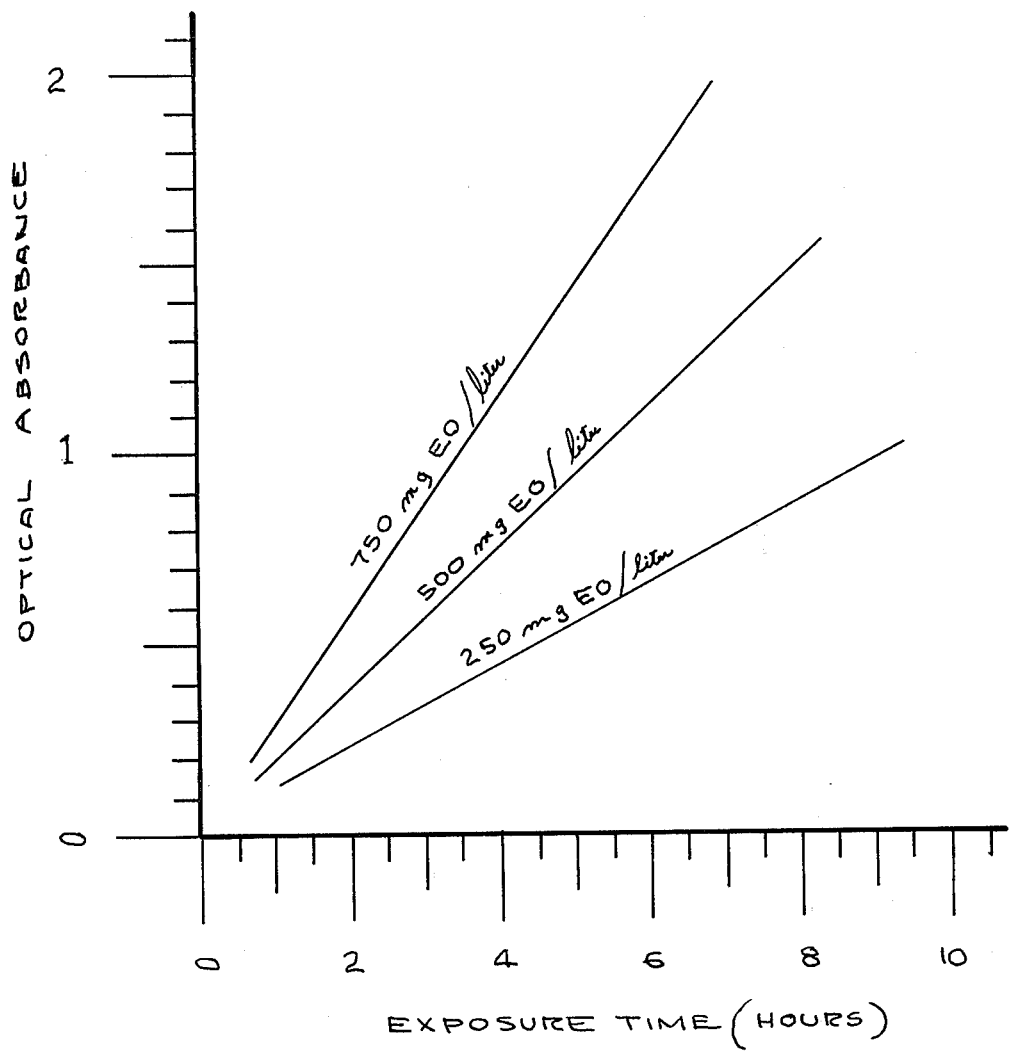
FIG. 1 is a graphic representation of the response of a device of this invention observed over time at constant ethylene oxide exposure.
Figure 2:
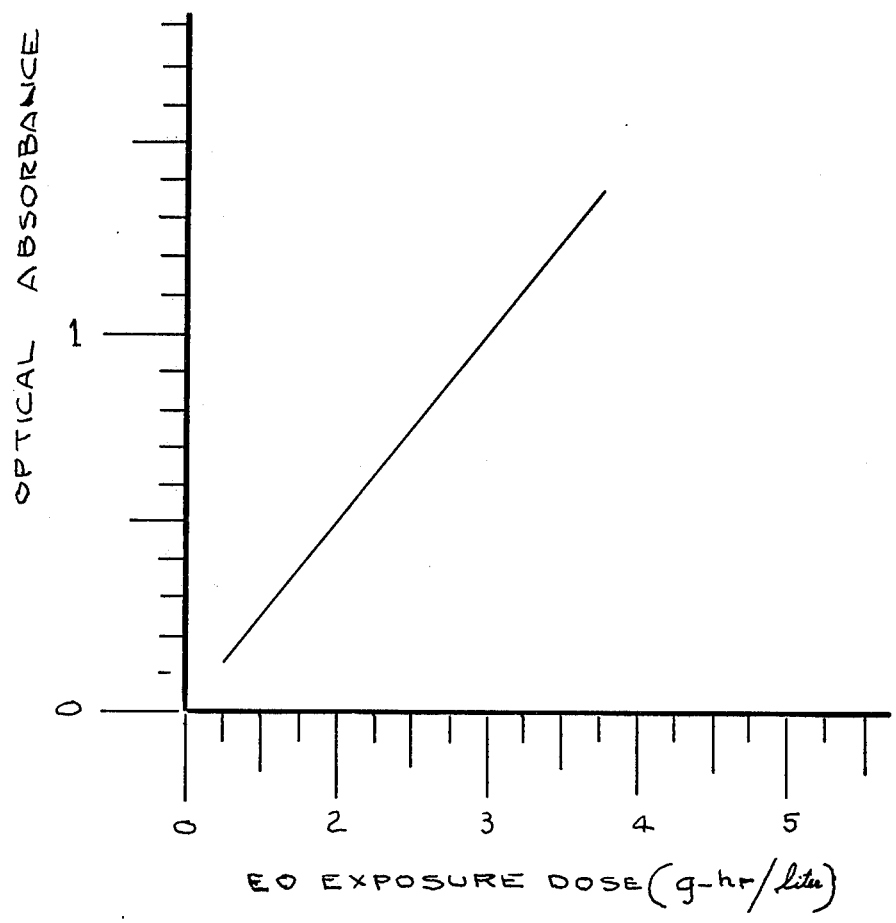
FIG. 2 is a graphic representation of device response with changing integrated exposure dose.
Figure 3:
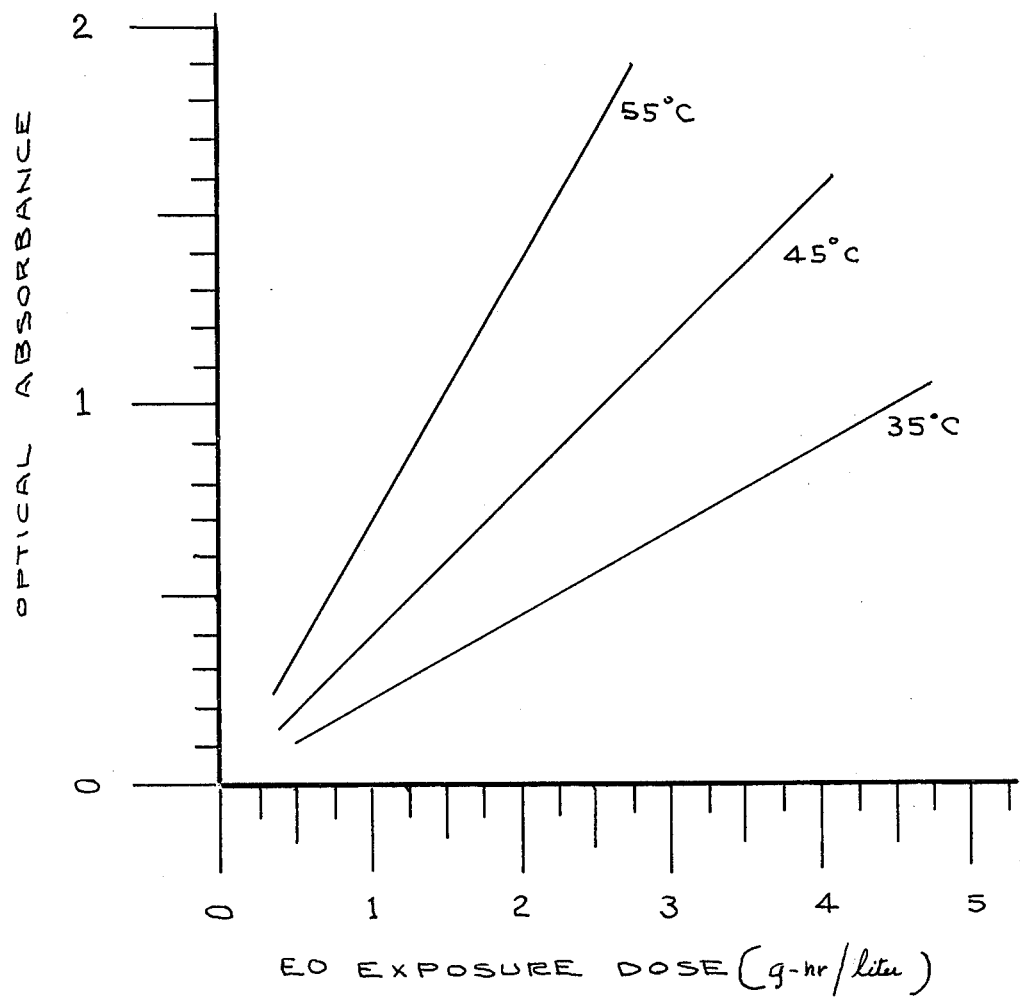
FIG. 3 is a graphic representation of device response rate as a function of exposure temperature.

These relationships are shown graphically in FIGS. 1, 2, and 3. In FIG. 1 the degree of color generation in devices of this invention, having been measured periodically over time by means of an absorbance measurement, is shown at three different constant ethylene oxide exposure concentrations. FIG. 2 shows the direct linear relationship between response (as measured by absorbance) and integrated exposure dose (Concentration×Exposure Time). Thus, this device can show in quantitative terms, the dose received by its environment such as during sterilization or the like. It should be clear that by measuring absorbance and knowing either the ethylene oxide concentration or the exposure time, the other could be determined from these graphs. Dosimeter response is dependent upon temperature. At high temperatures the response is greater than at lower temperatures. FIG. 3 shows graphically the relationship between dosimeter response rate and temperature. Typical laboratory data demonstrating dosimeter response as a function of exposure parameters are shown in Table 1.

TABLE 1

Laboratory Data Demonstrating Device Response As a Function of Ethylene Oxide Exposure Concentration, Exposure Time, and Exposure Temperature

| Sample | EO Concentration | Exposure Time | Temperature | Dosimeter Absorbance |
|---|---|---|---|---|
| 1 | 0.39 g/l | 1.0 hr | 45° C. | 0.17 |
| 2 | 0.39 g/l | 2.0 hr | 45° C. | 0.31 |
| 3 | 0.39 g/l | 3.0 hr | 45° C. | 0.50 |
| 4 | 0.39 g/l | 4.0 hr | 45° C. | 0.71 |
| 5 | 0.66 g/l | 1.0 hr | 45° C. | 0.25 |
| 6 | 0.66 g/l | 2.0 hr | 45° C. | 0.52 |
| 7 | 0.66 g/l | 3.0 hr | 45° C. | 0.85 |
| 8 | 0.66 g/l | 4.0 hr | 45° C. | 1.20 |
| 9 | 0.92 g/l | 1.0 hr | 45° C. | 0.31 |
| 10 | 0.92 g/l | 2.0 hr | 45° C. | 0.67 |
| 11 | 0.92 g/l | 3.0 hr | 45° C. | 1.10 |
| 12 | 0.92 g/l | 4.0 hr | 45° C. | 1.62 |
| 13 | 0.66 g/l | 1.0 | 35° C. | 0.14 |
| 14 | 0.66 g/l | 2.0 | 35° C. | 0.28 |
| 15 | 0.66 g/l | 3.0 | 35° C. | 0.44 |
| 16 | 0.66 g/l | 4.0 | 35° C. | 0.78 |
| 17 | 0.66 g/l | 1.0 | 55° C. | 0.33 |
| 18 | 0.66 g/l | 2.0 | 55° C. | 0.72 |
| 19 | 0.66 g/l | 3.0 | 55° C. | 1.12 |

The present device can also be used to measure ethylene oxide residual in an ethylene oxide-treated article.

In order to quantitatively determine the quantity of residuals present in an ethylene oxide-treated article, the device requires an adjunct device—an extraction container, and an external source of heat. The extraction container is a highly ethylene oxide-impermeable container which, when hermetically sealed, restricts escape of ethylene oxide which is volatilized from the article via heating. In use, the device and the item being tested are sealed in the extraction container and the container is heated. Alternately, two containers may be used, one in which the test article is heated to volatilize EO gas which is then transferred to a second container holding the residual test device.

The device itself is a "sink" or collector for ethylene oxide and works analogously to the process dosimeter.

Color generation within the device is accomplished by incorporation of a color-forming substance. The intensity of color generated is proportional to the quantity of ethylene oxide collected, which is, in turn, proportional to the quantity of ethylene oxide volatilized within the extraction pouch, which, itself, relates directly to the quantity of ethylene oxide residual in the test article being tested.

Figure 4:
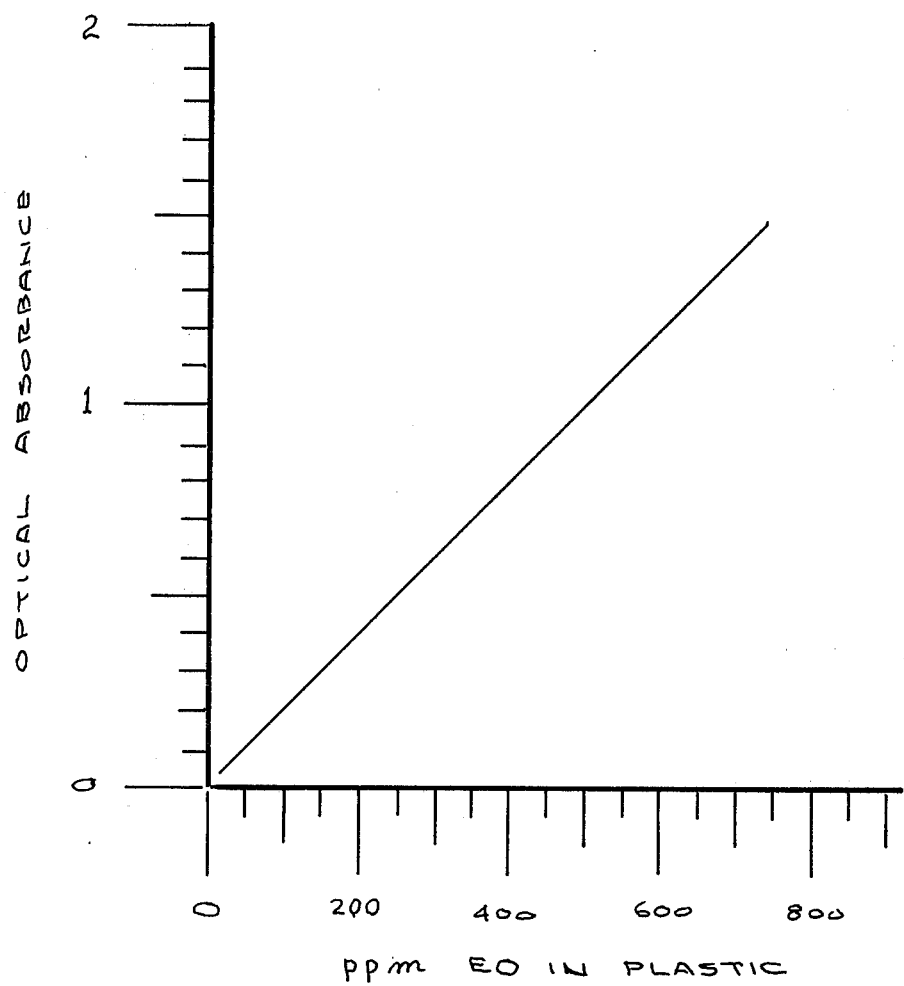
FIG. 4 is a graphic representation of device response when heated with an EO residual-bearing plastic.

The response of a device to levels of residual EO is demonstrated in FIG. 4.

Composition of Preferred Embodiments

The device of this invention provides a visual chemical indication of ethylene oxide exposure. It relies upon the property of a chemical herein referred to as a color-forming compound, to readily react with ethylene oxide and in that reaction to yield a color change. As a general rule, the chemicals that are employed should react with ethylene oxide at low temperatures, such as from about room temperature (20°-22° C.) through the usual temperatures in a sterilizing environment (30°-60° C.). The compounds that are employed are organic, nitrogen-containing compounds that form colored reaction products with ethylene oxide or products having altered ultraviolet absorption spectra. These nitrogen-containing compounds include 4-(p-nitrobenzyl)pyridine as well as amines including pyridines such as 2-(p-nitrobenzyl)pyridine, 2,4-bis(p-nitrobenzyl)pyridine, 2,4,6-tris(p-nitrobenzyl)pyridine, 4-(o-nitrobenzyl)pyridine, and N-phenylbenzyl-pyridine; quinolines such as lepidine as well as other nitrogen-containing organic compounds such as 2,6-diaminoacridine, acridine, phenazine, phenoxazine, phenothiazine, and carbazole. Among these representative materials 4-(p-nitrobenzyl)pyridine is most preferred. 4-(p-nitrobenzyl)pyridine may also be used in conjunction with a promoter or catalyst such as N,N'-bis(aminopropyl)-1,3-propanediamine, N,N,N',N'-tetra(methyl)-ethylene diamine, triethylenetetramine, triethylenediamine, ethanolamine or tris-(hydroxymethylamino)methane. Mixtures of two or more color-forming compounds may, of course, be used.

The color-forming compound is dispersed in a suitable support. The support should be essentially inert to ethylene oxide, should permit Case II transport (see later discussion) of ethylene oxide and should not be of a color that interferes with or masks determination of the color-producing reaction. The support generally is transparent.

The property of Case II transport or the like is important to the performance of the present device. Afrey, Turner and Lloyd in an article entitled "Transport of Organic Penetrant in Glassy Polymers" appearing in *The Journal of Polymer Science* C, 12, 240 (1966), (incorporated herein by reference) explained the concept of Case II transport. Under Case II conditions the quantity of penetrant sorbed varies with the first power of the time compared to the ½ power for Fickian (normal) transport. Thus, color generation, in the device of this application which follows quantity of EO sorbed, will be essentially a first order function of exposure time and a first order function of exposure level, i.e., it will respond proportionally to dose. Where color-forming compounds are impregnated into conventional supports, such as plastics exhibiting "normal" transport or paper, or the like, response may follow first power of exposure concentration but only follows the ½ power of time and thus does not indicate dose.

A support which sorbs ethylene oxide in quantity proportional to the first power of time and exposure concentration is defined to be a "Case II-Transport" support and to be a suitable support. Cellulose acetate is a representative Case II-transport support that is readily available and preferred. Other suitable materials include polystyrene, polycarbonates, and polyesters.

The color-forming chemical is dispersed through the support. Preferably the color former is dissolved in the support but it is also possible to distribute very finely divided particles of solid color-former throughout the volume of support, if desired.

The amount of color-forming chemical in the support should be a uniform known and/or reproducible amount. It should be chosen to provide a measurable degree of color change with the ethylene oxide exposure. Generally, amounts of color-forming chemical in the range of from 0.5 to 5%, preferably 2 to 4% by weight, based on the weight of support are employed.

The devices of this invention are often in the form of an essentially two dimensional film, tape, slip, sticker or the like. In these cases, it is often informative to express color-former amounts in terms of mg per square centimeter of device. In these terms, color former amounts of from 0.05 to 5 mg per square centimeter of device or support are employed with amounts of from 1 to 5 mg per square centimeter of device or support being preferred.

Figure 5:
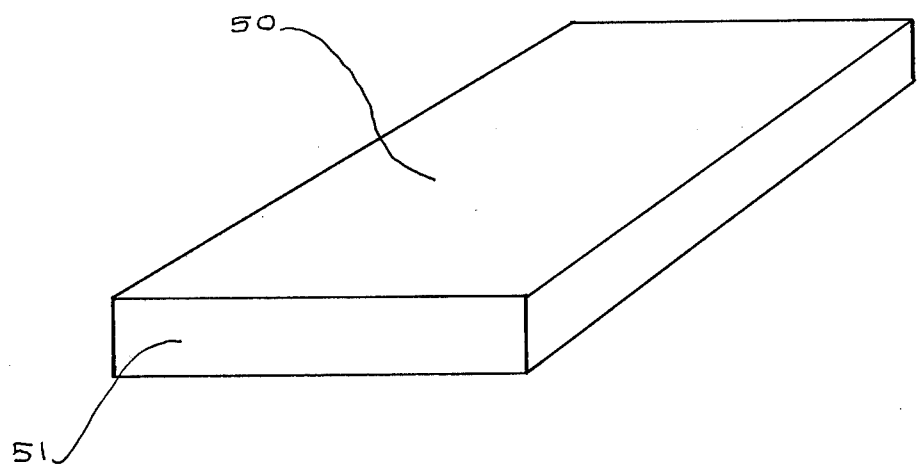
Figure 6:
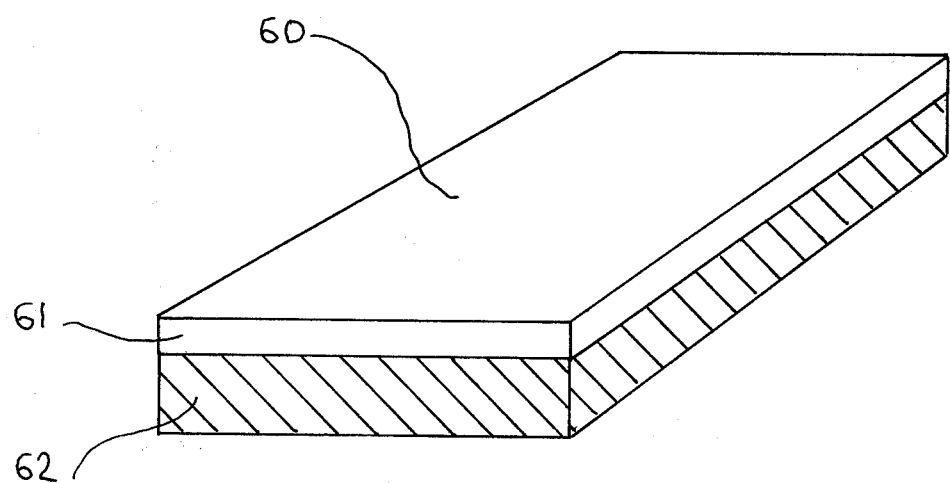

In its simplest form a device of this invention would consist essentially of a single layer of support with the color-forming compound dispersed through it, as depicted in FIG. 5 wherein the device 50 consists of a single layer 51. For some applications, it may be desirable to have additional layers in the device—such as a backing layer to provide means for strengthening or mounting or attaching the device in the environment of use. The backing layer, if present, should be of a material and thickness to be physically strong. It need not be permeable to ethylene oxide, although optionally it may have such permeability. The materials for the backing layer may include structural plastics such as polystyrene, polyvinyl chloride, polyolefins, acrylic polymers, polyesters, or polycarbonate, or the like. It may include material such as cardboard, paper or the like as well as inorganics such as glass, aluminums and the like. In general, the backing material should be chosen for its economy, its physical strength and its ease of fabrication rather than any more exotic properties. This embodiment is depicted in FIG. 6 wherein the device 60, response layer 61, and backing layer 62 are distinguished.

In an alternative construction, plastics which are permeable to ethylene oxide but which exhibit "normal" or Fickian transport may be fabricated into forms which exhibit dosimeter character (first order response to EO concentration and time of exposure). This is accomplished by creating a fixed-thickness diffusion layer of a Fickian transport plastic such as permeable polyethylene, polypropylene or silicone polymers and laminating one or two such diffusion layers to a central collector membrane that has a higher diffusion constant than the diffusion layer of two collector membranes laminated around a central response material in which the color-forming compound(s) is (are) contained. This embodiment is depicted in FIG. 7 wherein the device 70 is composed of a response layer 72 surrounded by collector layers 71 and 73 which may be similar or dissimilar materials.

The various layers may be laminated to one another or glued or otherwise bonded so long as the bonding does not interfere with the supports transport of ethylene oxide or the color-former's reaction with ethylene oxide. The devices of this invention and their use are further described with reference to the following examples. These are presented merely to exemplify the invention and are not intended as limitations in its scope.

EXAMPLES

Preparation A:

(1) Prepare a mixture of the following materials:
(a) 4-(p-nitrobenzyl)pyridine [0.001–0.1%]
(b) Methanol [1–10]
(c) Glycerol [0–25]
(d) Water [60–99]
(e) Tris (hydroxymethylamino)methane [0–5%].

(2) Immerse one or more sheets of a clear cellulose acetate plastic in the mixture from (1), above, and allow to stand for a fixed period of time, or until equilibrium sorption of the mixture from (1) by the plastic has been attained.

(3) After sorption, remove the plastic sheet(s) from the liquid mixture, rinse with water and/or alcohol, and wipe dry with a squeegee or soft cloth.

(4) Cut the plastic sheet(s) into chips of a size and shape appropriate to the intended application or process as shown in Preparation C.

Preparation B:

(1) Prepare a mixture of the following materials: Add in order indicated, and stir, with mild heating such as to 50° C., until a clear solution is achieved.
(a) Methanol [70–90%] or Methanol/Methylene Chloride mixture
(b) Polyethylene glycol or glycerol [0–30%]
(c) Hydroxpropyl cellulose or cellulose acetate (pellets or powder) [5–25%]
(d) Tris(hydroxymethylamino)methane [0–5%]
(e) Water [0–10%]
(f) 4-(p-nitrobenzyl)pyridine [2–20%]

(2) Cast the solution from (1), above, on a smooth, noncontaminating surface to make a layer of uniform thickness.

(3) Allow the casting to stand on a level plane at room temperature, or with heating, if desired, until a dry sheet results.

(4) Cut the plastic sheet(s) into chips of a size and shape appropriate to the intended application or further process as shown in Preparation C.

Preparation C:

(1) Laminate the response material sheets prepared in either Preparation A or Preparation B to one or two plastic films of the following type(s) using heat and/or pressure lamination, adhesive bonding, mechanical joining, or solvent or extrusion overcasting techniques.
(a) Polyolefin
(b) Polyester
(c) Ionomer
(d) Vinyl Polymer
(e) Halogenated Polyolefin
(f) Halogenated Vinyl
(g) Polycarbonate
(h) Acrylic Polymer
(i) Polyamide
(j) Cellulose Ester
(k) Polyphenylene
(l) Silicone Polymer

Preparation D:

(1) Prepare or purchase pouches or other hermetically sealable containers from sheets or films of material having very low gas permeability such as the following:
(a) Aluminum
(b) Polyethyleneterephthalate
(c) Halogenated polyolefin
(d) Halogenated vinyl polymer. These containers should be large enough to admit and enclose small objects that have been subjected to ethylene oxide sterilization.

Example I (Gas Treatment Process Exposure Dose Determination)

(1) Cut chips from the materials made in Preparations A through C of a size and shape which will enable them to be placed into a photometer for subsequent measurement of light absorbance.

(2) Place one or more of the chips from (1), above, into a chamber or flow stream used to sterilize, fumigate, or disinfect articles by ethylene oxide exposure.

(3) Expose the chip(s) along with the article(s) to be treated.

(4) At the end of the treatment, remove the chips and determine their optical absorbance by a suitable photometer, or visually by reference to standard colors. Alternately, treat the chip with a solution of basic catalyst prior to reading to enhance response.

(5) Determine the magnitude of treatment exposure in units of Agent Concentration (mg or g of ethylene oxide, etc.) times Exposure Time (hours, minutes, etc.) at a specified temperature by reference to a standard curve obtained from well-controlled exposures carried out at known concentrations, times, and temperatures. (FIG. 2 is an example of such a standard curve.)

(6) Where exposure time and temperature have been measured independently, Time×Average ethylene oxide concentration (i.e., total dosage) may be computed from a standard curve such as that shown in FIG. 1.

(7) Where exposure temperature has not been constantly controlled the combined integral indicative of exposure concentration, temperature, and time may be computed from the response on the exposure dose standard curve (FIG. 2) using the temperature curve (FIG. 3) for correction.

Example II (Residual Trace Ethylene Oxide Determination)

(1) Cut chips from Preparations A, B, C or D. The chips should be of a size and shape which will enable them to be placed into a photometer for subsequent measurement of light absorbance or reflectance.

(2) Place one chip from (1), above, along with an accurately determined quantity of some article which has previously been treated with ethylene oxide, into a pouch or container described as Preparation D.

(3) Hermetically seal the chip and article in the container and heat at a specified temperature (e.g. 70° C.) for a specified period of time, such as three hours.

(4) After treatment (3), above, remove the chip and determine its optical absorbance or reflectance by an appropriate photometer, or visually. Alternately, treat the chip with a solution of basic catalyst prior to reading to enhance response.

(5) By reference to a standard curve such as FIG. 4 prepared by similarly treating articles of known residual ethylene oxide content, one can compute the quantity of residual ethylene oxide present in the article under test.

I claim as my invention:

1. A device for colorimetrically quantifying exposure to ethylene oxide which comprises a polymer substrate which exhibits Case II-transport for ethylene oxide through the body of which is dispersed a concentration of a color-forming compound which undergoes a color-change upon reaction with ethylene oxide, said concentration being chosen to provide a variable degree of color-change in said device which, at a uniform temperature, is a previously determined function of the device's quantity of exposure to ethylene oxide.

2. The device of claim 1 wherein the substrate is selected from among the members of the group consisting of cellulose acetate, polycarbonate, polystyrene, and polyester.

3. The device of claim 1 wherein said color-forming compound comprises a material selected from the group of ethylene oxide-reactive color formers consisting of 4-(p-nitrobenzyl)pyridine, N-phenylbenzylpyridine and phenazine.

4. The device of claim 3 wherein said color-forming compound is 4-(p-nitrobenzyl)pyridine.

5. The device of claim 3 wherein the concentration of said color-forming compound is 0.5 to 5.0% by weight based on the weight of the substrate.

6. The device of claim 5 in an essentially two dimensional form.

7. The device of claim 6 consisting essentially of a single layer.

8. The device of claim 6 having a backing layer affixed thereto.

9. A method for quantifying an environment's exposure to ethylene oxide which comprises placing in said environment for a measuring period the device of claim 1, removing said device from said environment, measuring the degree of color change and relating the degree of color change to the environment's ethylene oxide exposure dose in units of (EO Concentration × Time).

10. The method of claim 9 wherein said environment comprises an ethylene oxide sterilization environment.

11. The method of claim 9 wherein said environment comprises a sealed container also containing an article bearing residual amounts of ethylene oxide to be determined.

12. The method of claim 9 wherein a basic catalyst is added to the device following ethylene oxide exposure to enhance color formation resulting from low level exposure.

13. The method of claim 12 wherein said basic catalyst is a member selected from the group consisting of triethanolamine, triethylenediamine, triethylenetetramine, N,N-bis(aminopropyl)-1,3-propanediamine, and N,N,N',N'-tetrakis(methyl)-ethylenediamine.

* * * * *